(12) United States Patent  (10) Patent No.: US 6,964,671 B2
Cheng et al.  (45) Date of Patent: Nov. 15, 2005

(54) METHOD AND APPARATUS FOR PLACING A MEDICAL AGENT INTO A VESSEL OF THE BODY

(75) Inventors: Eric Cheng, Miami, FL (US); Larry Dominguez, West Miami, FL (US); Ajay K. Wakhloo, Key Biscayne, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 641 days.

(21) Appl. No.: 09/894,421

(22) Filed: Jun. 28, 2001

(65) Prior Publication Data

US 2003/0004525 A1  Jan. 2, 2003

(51) Int. Cl.⁷ ............................................. A61M 29/00
(52) U.S. Cl. ........................ 606/200; 606/191; 606/195
(58) Field of Search ................................ 606/108, 190, 606/191, 194, 195, 198, 200; 623/1.1, 1.11, 623/1.15, 1.18, 1.22, 1.27; 604/93.01, 95.01, 604/95.03, 95.04, 95.05, 164.04, 164.13, 604/264, 266, 523–535, 290, 907

(56) References Cited

U.S. PATENT DOCUMENTS

| 2,688,329 A | 7/1954 | Wallace |
| 4,790,331 A | 12/1988 | Okada et al. |
| 5,108,407 A | 4/1992 | Geremia et al. |
| 5,122,136 A | 6/1992 | Guglielmi et al. |
| 5,263,964 A | 11/1993 | Purdy |
| 5,334,210 A | 8/1994 | Gianturco |
| 5,350,397 A | 9/1994 | Palermo et al. |
| 5,382,259 A | 1/1995 | Phelps et al. |
| 5,464,395 A | 11/1995 | Faxon et al. |
| 5,667,493 A | 9/1997 | Janacek |
| 5,776,114 A | 7/1998 | Frantzen et al. |
| 5,779,669 A | 7/1998 | Haissaguerre et al. |
| 5,836,957 A | 11/1998 | Schulz et al. |
| 5,846,223 A | 12/1998 | Swartz et al. |
| 5,853,418 A | 12/1998 | Ken et al. |
| 5,873,842 A | 2/1999 | Brennen et al. |
| 5,885,238 A | 3/1999 | Stevens et al. |
| 5,911,725 A | 6/1999 | Boury |
| 5,916,194 A | 6/1999 | Jacobsen et al. |
| 6,113,622 A | 9/2000 | Hieshima |
| 6,126,649 A | 10/2000 | VanTassel et al. |
| 6,179,857 B1 | 1/2001 | Diaz et al. |
| 6,183,491 B1 | 2/2001 | Lulo |

*Primary Examiner*—Henry Bennett
*Assistant Examiner*—Andrea M. Ragonese

(57) ABSTRACT

A method and apparatus for placing a medical agent, such as an embolic coil into a vessel, or aneurysm, by utilizing a stabilizing catheter to retain or support a medical agent deployment device.

1 Claim, 3 Drawing Sheets

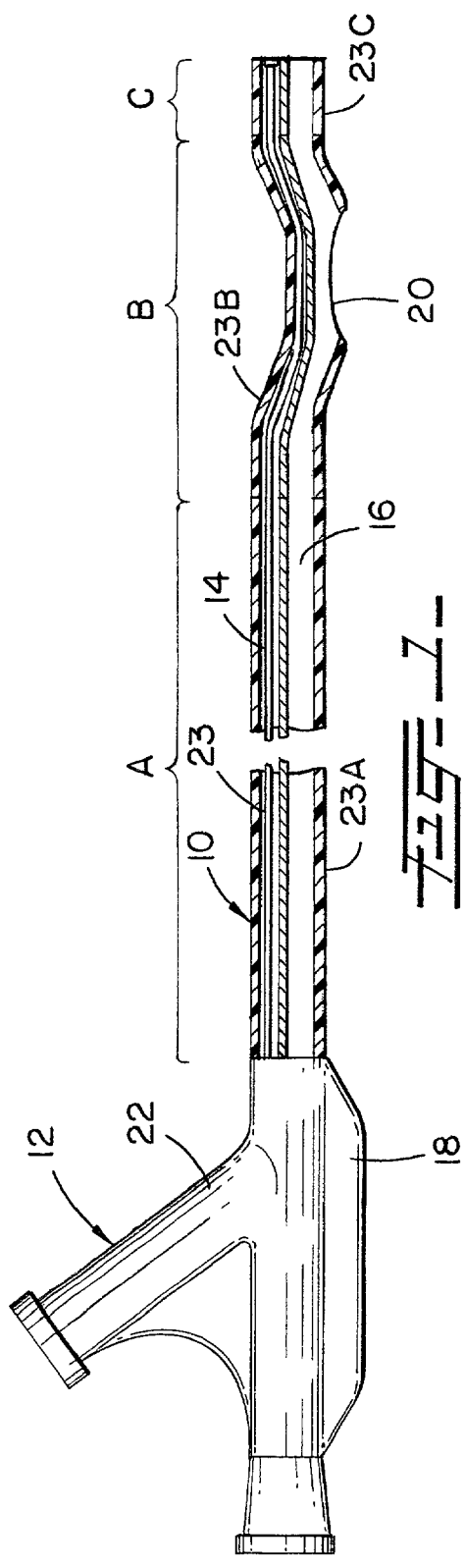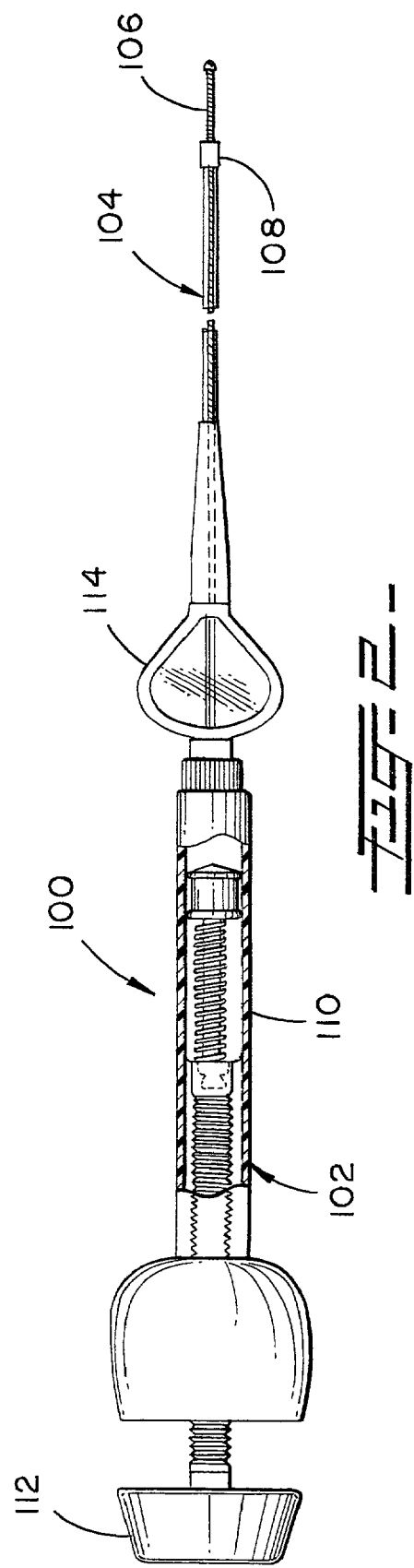

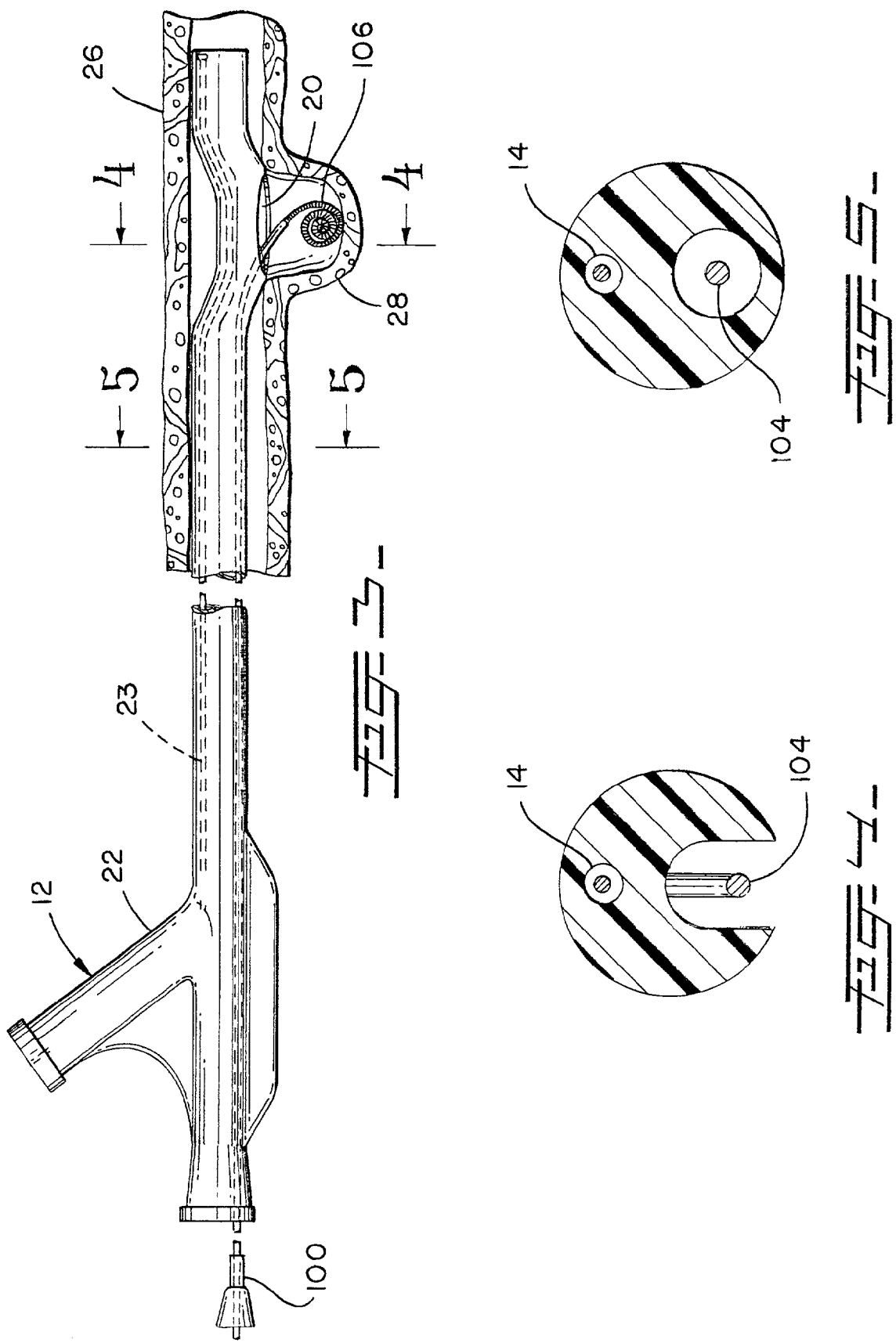

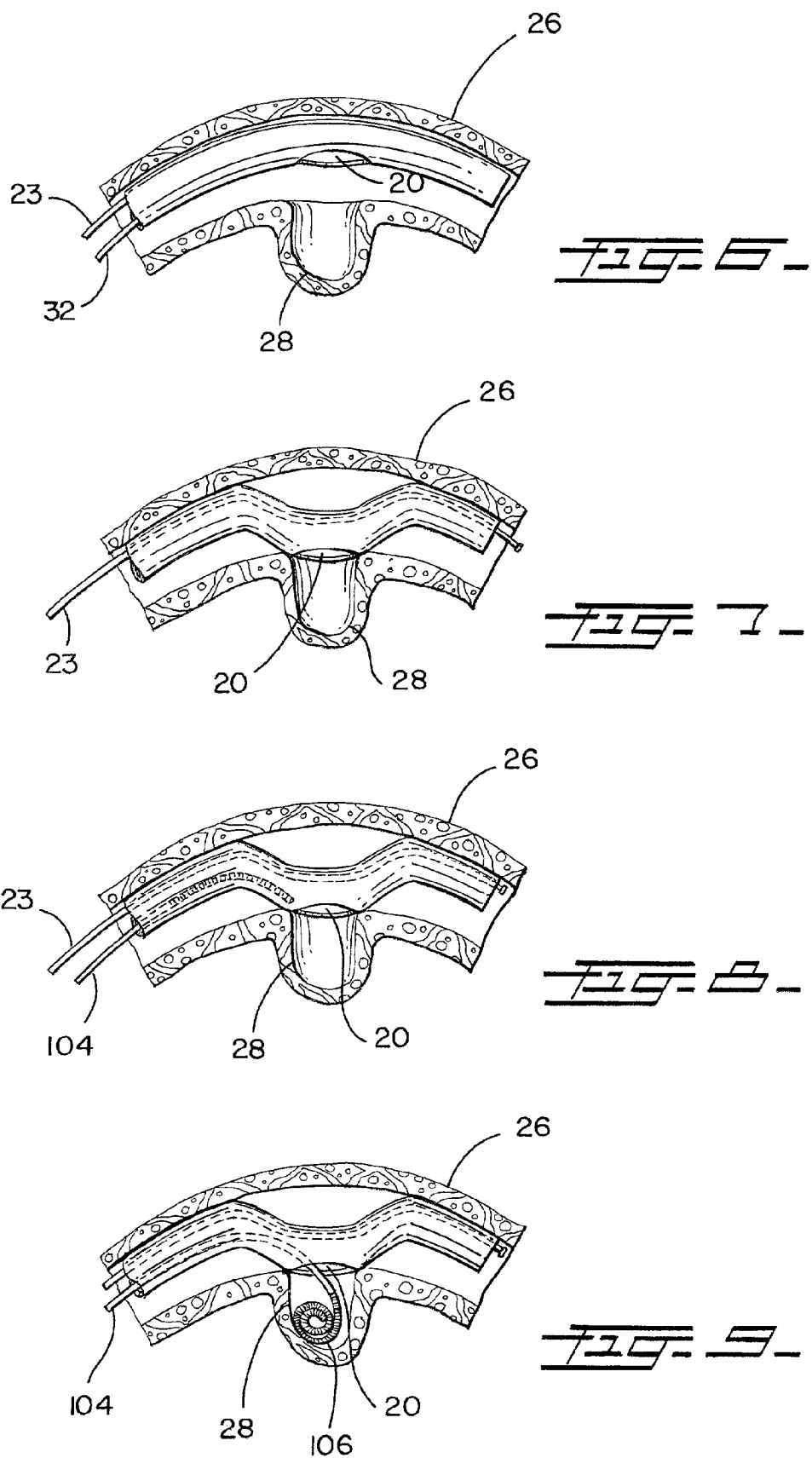

METHOD AND APPARATUS FOR PLACING A MEDICAL AGENT INTO A VESSEL OF THE BODY

BACKGROUND OF THE INVENTION

1. Field of the Invention

This invention concerns a novel method and apparatus for placing a medical agent into a vessel of the body, and in particular concerns a novel method for placing embolic coils within an aneurysm of the brain.

2. Description of the Prior Art

The use of embolic coils placed within an aneurysm for treating the aneurysm within the brain is well known. Various devices are known for delivering embolic coils through the patient's vessel to the aneurysm. Typically these embolic coils, which generally take the form of helically wound coils, or random wound coils, are carried by a coil deployment device which serves to introduce the coils into the aneurysm. The coils are then released by the coil deployment device using one of various types of release mechanisms.

An example of such a coil deployment device is disclosed in U.S. Pat. No. 6,113,622 entitled, "Embolic Coil Hydraulic Deployment System", issued Sep. 5, 2000 and assigned to the same assignee as the present patent application. The disclosure of this patent is incorporated herein and made a part of this application. It has been found to be difficult to place these coils in the exact desired position because of the relative lack of stability of the deployment device within the vessel during the introduction of the embolic coil to an aneurysm. An example of a delivery system used to stabilize a coil deployment device is disclosed in U.S. patent application Ser. No. 09/878,530, entitled "Delivery System Using Balloon Catheter", filed Jun. 11, 2001 and assigned to the same assignee as the present patent application. The disclosure in this patent application is incorporated by reference and is made a part of the subject patent application.

It is, therefore, an object of this invention to provide a method for placing embolic coils in a relatively precise manner by the use of a stabilizing delivery catheter.

Another object of the present invention is to provide a method for placing embolic coils within an aneurysm of the brain, which system is relatively simple in use for the physician.

A further object of the present invention is to provide a method for delivering medical agents such as diagnostic or therapeutic agents, and other medical agents by the use of a delivery catheter in a relatively simple, efficient and stable manner.

A still further object is to provide a delivery catheter which enables the delivery of embolic coils within an aneurysm in a relatively simple, efficient and stable manner.

Another object of the present invention is to provide a delivery catheter which may be utilized to deliver embolics, diagnostic, and therapeutic agents by way of a delivery lumen.

A further object of the present invention is to provide a delivery catheter that is relatively simple in construction.

Other objects of the present invention will become apparent from the following description.

SUMMARY OF THE INVENTION

In accordance with one aspect of the present invention, there is provided a method for placing an embolic coil into an aneurysm. The method includes the use of a delivery catheter having a proximal section, a distal section and an intermediate section which is formed from a very flexible polymeric material. The catheter includes a first lumen and a second lumen having a side opening at a location within the intermediate section of the delivery catheter. The catheter also includes a pre-shaped retaining wire which extends through the first lumen for shaping the intermediate section into a generally U-shaped configuration. The method includes the steps of inserting a straightening wire into the second lumen of the catheter to cause the intermediate section of the catheter to become relatively straight, introducing the delivery catheter into the vessel of a patient to generally align the side opening with an aneurysm, withdrawing the straightening wire from the second lumen to cause the intermediate section of the delivery catheter to return to the U-shaped configuration at a location proximal to the aneurysm to thereby cause the side opening to move to a position adjacent to the aneurysm, introducing an embolic coil deployment system into the proximal end of the delivery catheter through the second lumen and then through the side opening into the aneurysm. The method also includes the steps of delivering the embolic coil into the aneurysm with the coil deployment system, withdrawing the embolic coil deployment system from the delivery catheter, again inserting the straightening wire into the second lumen of the catheter to cause the intermediate section to become relatively straight, and thereafter withdrawing the delivery catheter from the vessel of the patient.

In accordance with the present invention there is also provided a method for placing a medical agent within a vessel. The method utilizes a delivery catheter having a proximal section, a distal section and an intermediate section which is formed of a polymeric material which is relatively flexible, and in which the intermediate section is normally shaped in a generally U-shaped, or bowed, configuration. In addition, the catheter has a first lumen and a second lumen having a side opening at a location within the intermediate section of the delivery catheter. The method includes the steps of inserting a guidewire into the second lumen of the catheter to thereby cause the intermediate section of the catheter to straighten, introducing the catheter into the vessel of a patient to generally align the side opening at a preselected position within the vessel, withdrawing the guidewire to thereby permit the intermediate section of the catheter to straighten, introducing a medical agent deployment device into the second lumen of the delivery catheter and through the side opening to deliver a medical agent at the preselected position, reinserting a guidewire into the second lumen of the delivery catheter to thereby again cause the intermediate section of the catheter to straighten, and thereafter withdrawing the delivery catheter from the vessel of the patient.

In accordance with still another aspect of the present invention, the medical agent takes the form of a diagnostic agent, a therapeutic agent or such device such as an embolic coil.

In accordance with still another aspect of the present invention there is provided a method for placing an embolic coil into an aneurysm. The method utilizes a delivery catheter which has a proximal section, a distal section and an intermediate section which is formed from a very flexible polymeric material. The intermediate section is normally shaped into a generally U-shaped, or bowed configuration. The catheter also includes a first lumen and a second lumen having a side opening at a location within the intermediate section of the delivery catheter. The method also incorporates a coil deployment device which includes an elongated flexible deployment catheter having a lumen extending therethrough and having a distal section being formed of a material of a durometer which exhibits the characteristics that when a fluid pressure is applied to the lumen of the deployment catheter the walls of the distal section expand outwardly. The coil deployment device in addition includes an embolic coil which is disposed in fluid tight engagement within the lumen o the distal section of the device. In addition, the coil deployment device includes a source of pressure coupled to the proximal section of the device for applying a fluid pressure to the lumen of the coil deployment device. The method includes the steps of inserting a straightening wire into the second lumen of the catheter to cause the intermediate section of the catheter to become relatively straight, introducing the delivery catheter into the vessel of a patient to generally align the second opening with an aneurysm, withdrawing the straightening wire from the second lumen of the delivery catheter to cause the intermediate section to return to the U-shaped configuration at a location proximal to the aneurysm to thereby cause the side opening to move to a position adjacent the aneurysm. The method also includes the steps of introducing the embolic coil deployment device into the proximal end of the delivery catheter through the second lumen and through the side opening into the aneurysm, applying a pressure with said source of pressure to the lumen of the deployment device to thereby cause the walls of the distal section of the deployment device to expand and release the embolic coil, withdrawing the embolic coil deployment device from the delivery catheter, again inserting the straightening wire into the second lumen of the catheter to cause the intermediate section to become relatively straight and thereafter withdrawing the delivery catheter from the vessel of the patient.

BRIEF DESCRIPTION OF THE DRAWINGS

FIG. 1 is a partial sectional view of a delivery catheter constructed in accordance with the principles of the present invention;

FIG. 2 is a partial sectional view of a vascular occlusive coil deployment system that may be used with the delivery catheter of FIG. 1;

FIG. 3 is a side elevational view of the delivery catheter of FIG. 1 in use to delivery an embolic coil to an aneurysm;

FIG. 4 is a cross-sectional view of the catheter of FIG. 3, taken along the plane of the line 5–5' of FIG. 3;

FIG. 5 is a cross-sectional view of the catheter of FIG. 3, taken along the plane of line 5–5' of FIG. 3; and, FIGS. 6 through 9 are diagrammatic sequential views of a method of placing embolic coils in accordance with an embodiment of the present invention.

DESCRIPTION OF THE PREFERRED EMBODIMENT

FIG. 1 generally illustrates the construction of a preferred embodiment of the delivery catheter of the present invention which generally comprises a dual lumen catheter 10 having a "Y" connector 12 coupled to the proximal end of the catheter. More particularly, the dual lumen catheter includes a first lumen 14 and a second lumen 16. The second lumen 16 extends from the proximal end of the catheter to the distal end of the catheter and also communicates with a lumen 18 which extends from the distal end to the proximal end of the "Y" connector 12. As illustrated, a side opening 20 extends from the second lumen 16 through the side wall of the catheter at a position which is slightly proximate the distal tip of the delivery catheter 10. This side opening, as will be subsequently explained in more detail, serves to permit the introduction of an embolic coil deployment device into an aneurysm for placement of an embolic coil into the aneurysm.

As further illustrated in FIG. 1, the first lumen 14 and a second lumen 16 extend through the delivery catheter 10. In addition, the proximal end of the first lumen 14 and the second lumen 16 communicate with passageways in the "Y" connector 12 and extend out of the side port 22 and the proximal end respectively of the "Y" connector 12.

While the delivery catheter 10 may be constructed of various flexible materials including various polymers, preferably, the catheter 10 is formed in three different sections of materials having different durometers and different polymer compositions. The proximal section of the catheter 23A, designated as "A", is preferably formed of a nylon material having a durometer of about 75 D and extends for a length of about 100 centimeters. The intermediate section 23B, designated as "B", is preferably formed of a pebax material having a durometer of about 40 D and is generally about 40 centimeters in length, and the distal section 23C of the catheter, designated as "C", is preferably formed of a pellethane material having a durometer of about 80A and extends for a length of about 10 centimeters. With this construction the catheter is sufficiently flexible to be delivered through the various tortuous vessels of the human brain but at the same time provides sufficient rigidity or "back-up" support for introducing the catheter into and through these vessels. This construction also makes possible the ease of deflection, or bowing, of the intermediate section 23B.

As may be seen, the delivery catheter also includes a pre-shaped wire 23 which is disposed in the first lumen 14. The wire 23 is bent, or bowed, in the region of the intermediate section to thereby cause the intermediate section to be bowed thereby causing the side opening to be moved laterally away from the center line of the catheter.

FIG. 2 illustrates a hydraulic occlusive coil deployment device 100 which is comprised of a hydraulic injector, or syringe, 102, coupled to the proximal end of a positioning catheter 104. An embolic coil 106 is disposed within the lumen at the distal section 108 of the catheter. The proximal end of the coil 106 is tightly held within the lumen of the distal section 108 of the catheter 104 until the deployment device is activated for release of the coil. As may be seen, the syringe 102 includes a threaded piston 110 which is controlled by the handle 112 for infusing fluid into the interior of the catheter 104. Also, as illustrated, the catheter 104 includes a winged hub 114 which aids in the insertion of the catheter.

The embolic coil 106 may take various forms and configurations, and may even take the form of a randomly wound coil. Preferably, the distal section of the coil deployment device 100 is formed of a polymeric material with a relatively low durometer which exhibits the characteristic that, when a fluid pressure of approximately 300 psi is applied to the interior of the catheter, the walls of the distal section 108 expand radially, somewhat similar to the action of a balloon inflating, to thereby release the proximal end of the coil 106. Reference is made to the above-mentioned U.S. Pat. No. 6,113,622 for a more detailed description of the hydraulic occlusive coil deployment device 100.

FIG. 3 illustrates in detail the delivery catheter 10 which has been inserted into a blood vessel 26 of the brain in order to place an embolic coil 106 into an aneurysm 28. FIGS. 4 and 5 illustrate cross-sections taken through the delivery catheter 10 at locations indicated by 4–4' prime and 5–5', respectively, shown in FIG. 3.

More particularly, FIG. 4 in conjunction with FIG. 3 illustrates the location where the pre-shaped wire 23 is bowed to cause the delivery catheter to be normally shaped in a generally U-shaped configuration at the intermediate section 23B of the catheter. Also illustrated in FIG. 4 is an end view of the embolic coil deployment device which extends through the side opening 20 of the catheter 10. FIG. 5 illustrates a sectional view of the delivery catheter 10 with the pre-shaped wire 23 disposed in the first lumen 14.

Reference is made to FIGS. 3 and 6 through 9 for an understanding of the operation of the delivery catheter used in conjunction with the embolic coil deployment device 100. As illustrated in FIG. 6, the delivery catheter is inserted into a vessel, over a stiffening guidewire 32, and is positioned such that the side opening 20 is adjacent to an aneurysm 28. The guidewire 32 is then removed and as illustrated in FIG. 7, the delivery catheter 10 deflects, or bows, in the region where the side opening 20 is located to thereby cause the side opening to essentially mate with the opening of the aneurysm 28. Once the side opening 20 has been positioned at the mouth of the aneurysm 28, the embolic coil deployment device 100 may then be inserted through the second lumen and then out of the side opening 20 and into the aneurysm 28 as illustrated in FIG. 8. Then the embolic coil 106 may be placed into the aneurysm and released from the distal end of the deployment device 100.

The deployment device 100 may then be removed and this process may be repeated until such time as sufficient coils have been placed into the aneurysm. When the aneurysm 28 has been sufficiently filled with embolic coils, the coil deployment device may be removed from the delivery catheter. Thereafter, the stiffening guidewire 32 may be inserted into the second lumen 16 to thereby cause the delivery catheter to straighten within the vessel. Once the catheter has straightened, the catheter may be easily withdrawn from the vessel and from the body of the patient.

Alternatively, the delivery catheter may be constructed with a shape retaining wire disposed in the first lumen 14 as opposed to the pre-shaped wire 23, and in this case the physician may pre-shape the intermediate section 23B into a generally U-shaped configuration prior to use.

In still another alternative construction, the delivery catheter may be a single lumen catheter having neither a pre-shaped wire 23 nor a shape retaining wire, but the catheter body is formed of a shape retaining polymer which may be heat set to form a U-shaped intermediate section, either when the catheter is manufactured or by the physician prior to use by the physician.

As may be appreciated, with the present invention it is possible to stabilize the delivery catheter at a position where the side opening of the delivery catheter is adjacent to the aneurysm. Embolic coils may be delivered through the side opening of the delivery catheter directly into the aneurysm with relatively good precision. With this system it is possible to fill an aneurysm with a plurality of embolic coils in very short order without the loss of coils into the main blood vessel, or other vessels within the body. These and other advantageous of this invention will become more apparent from an understanding of the invention as claimed.

A novel system and method have been disclosed in which an embolic coil, or coils, may be securely placed within an aneurysm with a delivery catheter which is stabilized. Although an illustrative embodiment of the invention has been shown and described, it is to be understood that various modifications and substitutions may be made by those skilled in the art without departing from the spirit and scope of the present invention.

Further, in addition to the delivery of embolic coils, the system may be utilized to deliver other medical agents such as diagnostic or therapeutic agents of various types including liquid embolic materials. Other modifications may be made which would be within the spirit and the scope of the following claims.

What is claimed is:

1. A method for placing an embolic coil into an aneurysm comprising the steps of:

providing a delivery catheter having a proximal section, a distal section and an intermediate section which is formed from a relatively flexible polymeric material, said catheter having a first lumen and a second lumen with a side opening from the second lumen at a location within the intermediate section, and said catheter having a pre-shaped retaining wire extending through said first lumen for normally forming the intermediate section into a generally U-shaped configuration;

inserting a straightening wire into the second lumen of the delivery catheter to cause said intermediate section of the catheter to become relatively straight;

introducing the delivery catheter into the vessel of a patient to generally align the side opening with the aneurysm;

withdrawing the straightening wire from said second lumen of said delivery catheter to cause the intermediate section of the delivery catheter to return to the U-shaped configuration at a location proximal to the aneurysm to thereby cause the side opening to move to a position adjacent to the aneurysm;

introducing an embolic coil deployment device into the delivery catheter through the second lumen and through the side opening into the aneurysm;

delivering the embolic coil into the aneurysm with the coil deployment device;

withdrawing the embolic coil deployment device from the delivery catheter;

again inserting the straightening wire into the second lumen of the catheter to cause said intermediate section to become relatively straight; and, thereafter withdrawing the delivery catheter from the vessel of the patient.

\* \* \* \* \*